United States Patent
McDonald

(10) Patent No.: US 8,425,228 B2
(45) Date of Patent: *Apr. 23, 2013

(54) DENTAL WEDGE

(75) Inventor: Simon P. McDonald, Katikati (NZ)

(73) Assignee: Triodent Holdings Limited, Katikati (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 13/490,340

(22) Filed: Jun. 6, 2012

(65) Prior Publication Data

US 2013/0034827 A1    Feb. 7, 2013

Related U.S. Application Data

(63) Continuation of application No. 11/703,189, filed on Feb. 7, 2007, now Pat. No. 8,206,151.

(30) Foreign Application Priority Data

Feb. 7, 2006   (NZ) ........................................ 545121
Sep. 1, 2006   (NZ) ........................................ 549580

(51) Int. Cl.
*A61C 7/00*   (2006.01)
*A61C 5/04*   (2006.01)

(52) U.S. Cl.
USPC .............................. 433/149; 433/39; 433/148

(58) Field of Classification Search .......... 433/147–149, 433/215–216, 39–40; 132/321–329
See application file for complete search history.

(56) References Cited

U.S. PATENT DOCUMENTS

| 2,008,206 | A | * | 7/1935 | Grant ............................. 132/329 |
| 2,867,905 | A |   | 1/1959 | Meacham |
| 2,891,313 | A |   | 6/1959 | Crowley |
| 3,193,094 | A | * | 7/1965 | Schulstad .................... 206/63.5 |
| 3,473,226 | A |   | 10/1969 | Arlers et al. |
| 3,510,948 | A |   | 5/1970 | Walthall |
| 3,636,631 | A |   | 1/1972 | Tofflemire |
| 3,815,243 | A |   | 6/1974 | Eames |
| 3,890,714 | A | * | 6/1975 | Gores .......................... 433/149 |
| 4,337,041 | A | * | 6/1982 | Harsany ....................... 433/149 |
| 4,468,199 | A |   | 8/1984 | Weikel |
| 4,570,653 | A | * | 2/1986 | Wolf ............................. 132/329 |
| 4,631,030 | A |   | 12/1986 | von Weissenfluh |
| 4,878,508 | A | * | 11/1989 | Durbin ......................... 132/329 |
| 5,507,646 | A | * | 4/1996 | Roth ............................ 433/216 |
| 5,527,181 | A |   | 6/1996 | Rawls et al. |
| 5,775,346 | A | * | 7/1998 | Szyszkowski ................ 132/329 |

(Continued)

OTHER PUBLICATIONS

European Patent Office, Partial European Search Report, European Patent Application No. EP 1815819A1, May 9, 2007, corresponding to U.S. Appl. No. 13/490,340 and related US Patent No. 8,206,151.

*Primary Examiner* — Yogesh Patel
(74) *Attorney, Agent, or Firm* — IpHorgan Ltd.

(57) ABSTRACT

A dental wedge for use in the inter-proximal space between adjacent teeth is described. The wedge comprises a taper section ending at a tip, and a body section extending to the tapering section at one end. The body section has an inverted V-shaped cross-section, flexing of the sides of the V-shape allows the wedge to adapt to various contours of the inter-proximal space. The mid-portion of the body section is narrower than at least a portion of the wedge either end of the mid-portion.

25 Claims, 12 Drawing Sheets

U.S. PATENT DOCUMENTS

| | | |
|---|---|---|
| 5,890,900 A | 4/1999 | Fischer et al. |
| 5,890,901 A | 4/1999 | Fischer et al. |
| 6,074,210 A | 6/2000 | Garrison |
| 6,402,514 B1 | 6/2002 | Fischer et al. |
| 6,482,007 B2 | 11/2002 | Stanwich et al. |
| 6,761,562 B2 * | 7/2004 | Von Weissenfluh ......... 433/149 |
| 6,890,176 B2 * | 5/2005 | Hahn .............................. 433/39 |
| 7,223,101 B2 | 5/2007 | Garrison et al. |
| 2002/0055084 A1 * | 5/2002 | Fischer et al. ................ 433/149 |
| 2003/0113688 A1 * | 6/2003 | Weissenfluh .................. 433/149 |
| 2004/0014006 A1 * | 1/2004 | Garrison et al. ............. 433/149 |
| 2005/0272005 A1 | 12/2005 | Schaffner et al. |

\* cited by examiner

DENTAL WEDGE

FIELD OF THE INVENTION

The present invention relates to an apparatus for use with dental matrixes in the placement of dental fillings.

SUMMARY OF THE PRIOR ART

To enable the dental professional to place composite fillings, matrixes are used. A matrix is a device which wraps around the tooth and acts as a mould to contain composite resins before they are cured. Matrices are generally formed of plastic or stainless steel and are either circumferential or sectional. Sectional matrices fit only in one proximal area of the tooth while circumferential matrix bands fit around the entire circumference of the tooth. Matrixes are secured in place by the use of wedges and/or clamps. The prior art wedges are generally made of wood or plastic and are placed between the matrix and an adjacent tooth. Wedges are used to hold the matrix against the tooth being filled and to temporarily separate the tooth being filled and the adjacent tooth. In the prior art wedges are not flexible or appropriately shaped and often cause punctures to the soft tissues and so are traumatic. Local anesthetics are often required.

As used herein the term "and/or" means "and" or "or", or both.

As used herein "(s)" following a noun means the plural and/or singular forms of the noun.

The term "comprising" as used in this specification and claims means "consisting at least in part of". When interpreting statements in this specification and claims which include that term, the features, prefaced by that term in each statement, all need to be present but other features can also be present. Related terms such as "comprise" and "comprised" are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7).

The entire disclosures of all applications, patents and publications, cited above and below, if any, are hereby incorporated by reference.

SUMMARY OF THE INVENTION

It is therefore an object of the present invention to provide a wedge for securing dental matrices which is an improvement on the prior art systems and devices or which will at least provide the industry with a useful choice.

The present invention may be said to consist in a dental wedge, for use in the inter-proximal space between adjacent teeth, comprising a taper section ending at a tip, a body section extending to said tapering section at one end, wherein said body section has an inverted V-shaped cross-section, flexing of the sides of the V-shape allowing the wedge to adapt to various contours of the inter-proximal space, and a mid-portion of said body section is narrower than at least a portion of the wedge either end of said mid-portion.

Preferably said body section, as viewed from said side is of substantially uniform depth.

Preferably said wedge includes a handle and said body section extends between said handle at one end and said tapered section at the other end.

Preferably said body section, viewed from a side, has a curved profile, rising to the handle and taper section, and curved downward toward said mid-portion.

Preferably handle comprises a flat member with a hole therethrough

Preferably the V-shaped cross-section is continuous along the length of said body section and taper section.

Preferably the contour of said wedge transitions smoothly along the length of the wedge.

Preferably said tip is blunt, with a leading end radius greater than 0.2 mm, and being at least 1.3 min wide 3 mm from said tip.

Preferably the side faces of said V-shaped cross-section are concave.

Preferably said sides can flex elastically toward each other during insertion through a space narrower than the widest width of said wedge.

Preferably the length of said wedge, excluding the handle, is between 10 mm and 20 mm.

Preferably the maximum width of said wedge, excluding said handle, is between 0.8 mm and 3.6 mm.

Preferably the height of a cross-section of said wedge in said body section is between 1.2 mm and 2.4 mm.

Preferably at its lowest point along the wedge, the upper edge of the wedge (excluding any handle) is spaced between 0.6 mm and 1.1 mm from a line extending between the upper edge of the wedge adjacent the tip and the upper edge of the wedge adjacent the handle.

Preferably said V-shaped cross-section includes an angle of between 50° and 25° at the most open cross-section.

Preferably said V-shaped cross-section at said mid-portion includes an angle of between 35° and 15°.

In a second embodiment the present invention may be said to consist in a dental wedge, for use in the inter-proximal space between adjacent teeth, comprising a taper section ending at a tip, a body section extending to said tapering section at one end, wherein said body section has an inverted V-shaped cross-section, flexing of the sides of the V-shape allowing the wedge to adapt to various contours of the inter-proximal space, and said body section, when viewed from a side, has a curved profile, rising to said taper section and the end opposite said tapered section, and curved downward toward a mid-portion.

Preferably said wedge includes a handle and said body section extends between said handle at one end and said tapered section at the other end.

In a third embodiment the present invention may be said to consist in a dental wedge, for use in the inter-proximal space between adjacent teeth, comprising a taper section ending at a tip, a body section extending to said tapering section at one end, wherein said body section and said tapered section comprise a pair of sidewalls converging to form an upwardly facing ridge, flexing of the sidewalls allowing the wedge to adapt to various contours of the inter-proximal space, and said body section, when viewed from a side, has a curved profile, rising to said taper section and the end opposite said tapered section, and curved downward toward a mid-portion.

Preferably said body section is of substantially consistent height along said body section.

Preferably said sidewalls are steeper at said mid-portion than at regions toward either end of said wedge.

In a third embodiment the present invention may be said to consist a dental repair site comprising a pair of adjacent teeth, an inter-proximal space between said teeth, a cavity, prepared for filling, facing said inter-proximal space, a dental matrix in said inter-proximal space, dividing said teeth and forming a mold for a filling of said cavity, and a wedge as claimed in any one of claims 1 to 21 including a handle passing through said inter-proximal space adjacent the gingival tissue, with said handle protruding at one side with said tip protruding at the other side and said handle and tip rising away from said gingival tissue, and a side of the body section pressing against a lower portion of said dental matrix.

In this specification, where reference has been made to external sources of information, including patent specifications and other documents, this is generally for the purpose of providing a context for discussing the features of the present invention. Unless stated otherwise, reference to such sources of information is not to be construed, in any jurisdiction, as an admission that such sources of information are prior art or form part of the common general knowledge in the art.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

BRIEF DESCRIPTION OF THE DRAWINGS

Preferred forms of the present invention will now be described with reference to the accompanying drawings in which.

DETAILED DESCRIPTION OF THE PRESENT INVENTION

Figure 1:
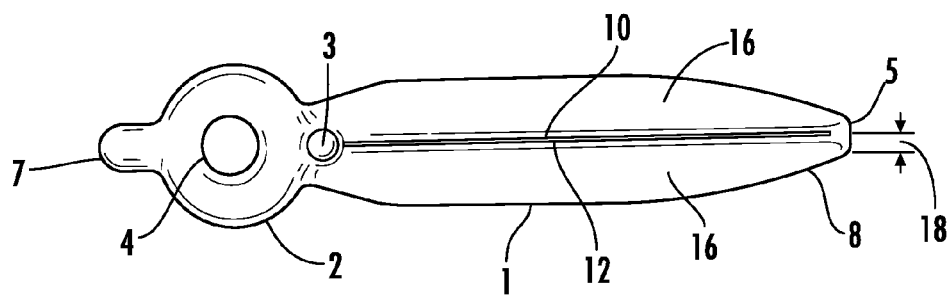
FIG. 1 is a plan view of the dental wedge of the present invention.

Referring to FIG. 1 the wedge comprises a one piece member of semi-hard or hard plastic or thermoplastic and has three main parts, a body section 1, a tapered end section 8 and a handle section 2. The wedge has a ridge 10 and two sides 16 and 16' converging towards the ridge. The ridge 10 runs along the top of the body section 1 and tapered end 8.

Figure 2:
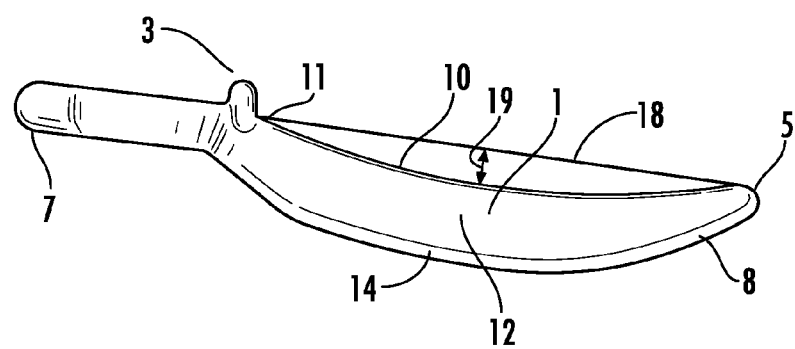
FIG. 2 is a side view of the dental wedge of the present invention.

Referring to FIG. 2 the body section 1 when viewed from the side has a curved profile. The ridge 10 of the body section 1 rises from the centre 12 of the body section 1 to the handle end 11 of the body section 1 and at the opposite end to the tapered end section 8

The tip 5 of the tapered end section 8 is blunt to help prevent damage when the wedge is inserted between teeth. The leading end radius 18 of the tip 5 of the tapered end 8 is greater than 0.2 mm, with the wedge tapering out, so that it is at least 1.3 mm wide 3 mm from the tip 5.

The wedge between the tip 5 and adjacent the handle 11 is between 10 mm and 20 mm long. At the lowest point along the ridge 10, the upper edge or ridge 10 of the wedge (excluding any handle) is spaced 19 between 0.6 mm and 1.8 mm from a line 18 extending between the upper edge or ridge 10 of the wedge adjacent the tip 5 and the upper edge of the wedge adjacent the handle 11.

Figure 3:
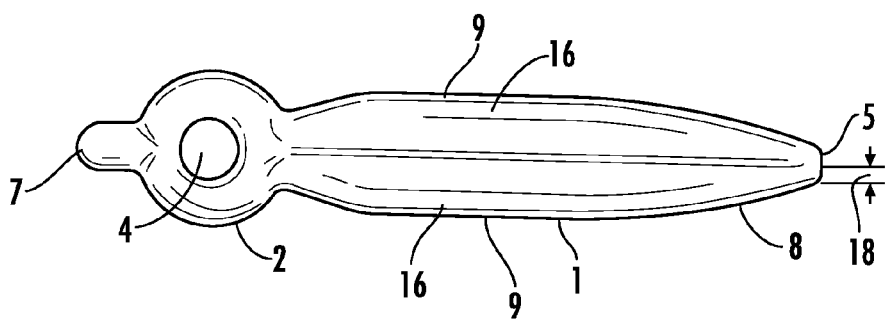
FIG. 3 is a bottom view of the dental wedge of the present invention.
Figure 4:
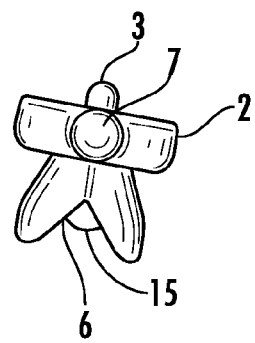
FIG. 4 is an end view of the dental wedge of the present invention.
Figure 5:
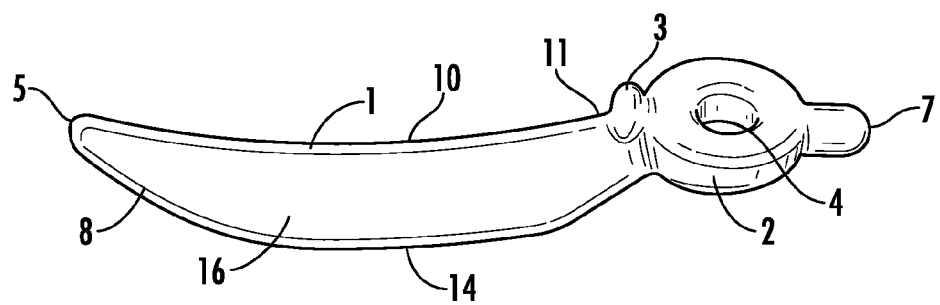
FIG. 5 is an orthogonal view from the side of the dental wedge of the present invention.
Figure 6:
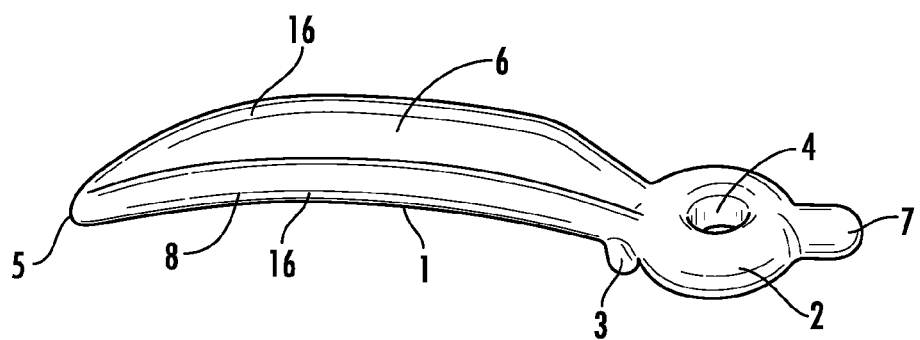
FIG. 6 is an orthogonal view from the bottom of the dental wedge of the present invention.
Figure 7:
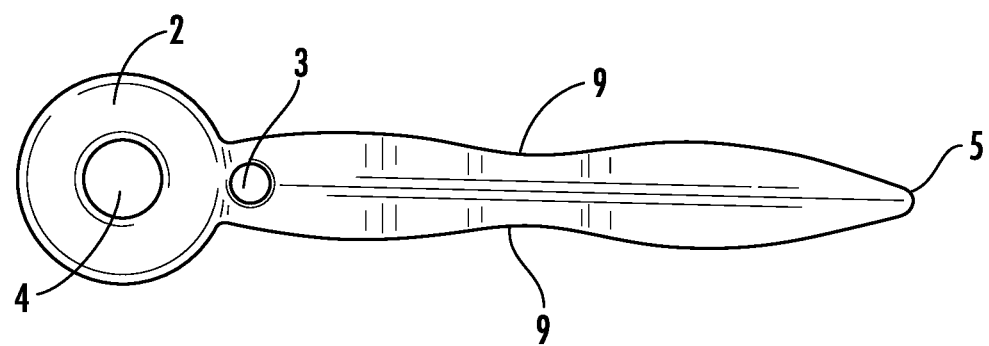
FIG. 7 is a plan view of an alternate embodiment of the dental wedge of the present invention.
Figure 8:
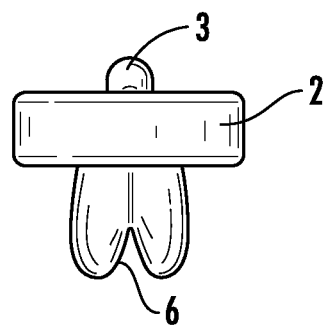
FIG. 8 is an end view of the dental wedge of FIG. 7.
Figure 9:
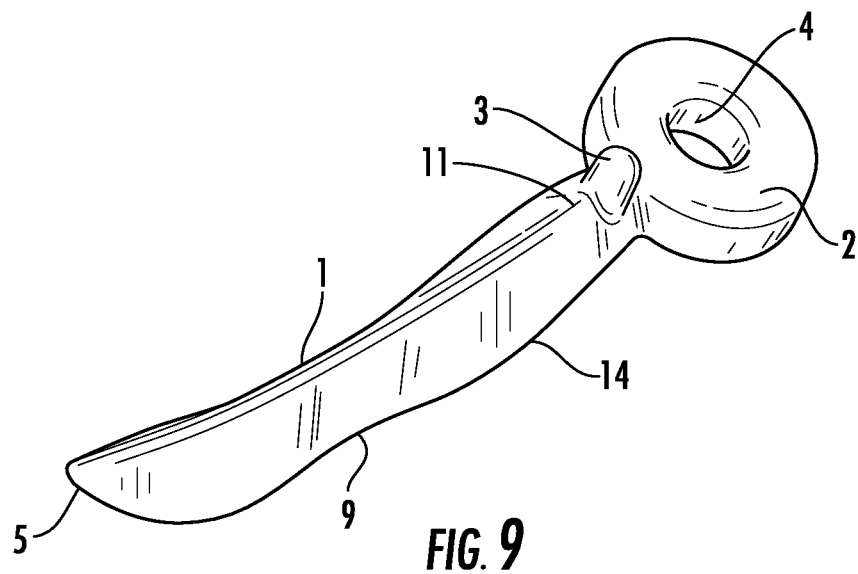
FIG. 9 is an orthogonal view from the top of the dental wedge of FIG. 7.
Figure 10:
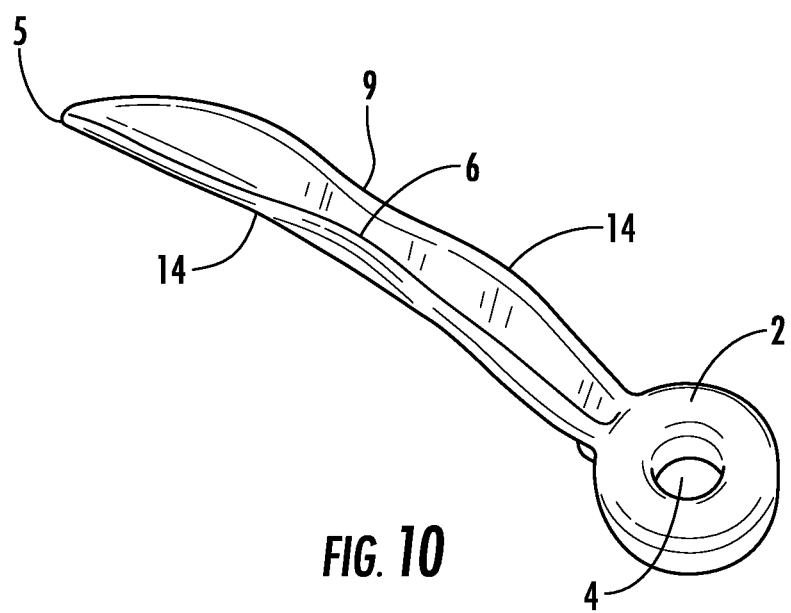
FIG. 10 is an orthogonal view from the bottom of the dental wedge of FIG. 7.

Referring to FIG. 3 the when viewed from the underside the wedge has a hollow 6. The wedge body 1 in cross section as seen in FIG. 4 is an inverted V shape. The sides of the wedge body 16 rise to the ridge 10. The angle 15 of the V-shaped cross section is between 25 degrees and 50 degrees at the most open cross-section. The V shaped cross section may extend to the tapered end section 8. The sides 16 of the wedge are sufficiently flexible to flex together as the wedge is inserted into the inter-proximal space. The side faces of the sides 16 are optional concave.

The optional handle 2 is flat member and optionally has a hole 4 in the centre. The handle optionally further has a cylindrical protrusion 7 at the opposite side of the handle 2 to the wedge body 1 to assist in removing the wedge. An optional cylindrical protrusion 3 on the ridge 10 between the handle 2 and the body section 1 may assist in removing the wedge.

In the embodiment of the wedge illustrated in FIGS. 1 to 6 a mid section/portion 9 of the body section 1 the bottom 14 of the side walls 16 are parallel for a least a portion of the wedge body 1 length. The height/depth of the wedge between the ridge 10 and the bottom 14 of the side walls is substantially the same height along the body section 1. In particular the mid section/portion 9 between the ridge 10 and the bottom 14 of the side walls is substantially the same height.

The wedge may be made in various versions from soft to hard. The materials to be used may include Santoprene™ thermoplastic vulcanizates from Advanced Elastomer Systems for a soft wedge, polypropylene for a hard wedge and polyethylene for a mid version.

In an alternate embodiment seen in FIGS. 7 to 10 the wedge body 1 has a narrow mid section/portion 9. The narrow mid-portion/mid-section 9 is designed to replicate the inter-proximal space more accurately. The wedge with a narrow mid section/portion 9 when viewed in a plan view looks like a wave. The contour of the wedge transitions smoothly between the different width sections.

Further embodiments of the wave wedge can be seen in FIGS. 13 to 27. Different thickness of the wedge and the wedge mid portions are desirable so that the appropriate wedge can be used depending on the inter-proximal space between teeth.

Referring to FIGS. 13 to 17 a medium sized wedge is illustrated. The wedge body 1 has three distinct widths, the mid-portion, between the mid-portion 9 and the tapered end 8 of the body and between the mid-portion 9 and the handle end 11 of the body 1. The second or third width is the widest point of the wedge. In general the second and third cross sections will be the same width but they may be of different width.

Figure 16:
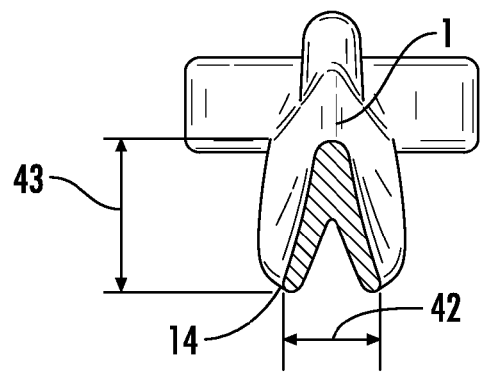
FIG. 16 is a cross section along the line C-C of the dental wedge of FIG. 13.

The mid portion 9 is the narrowest portion of the body 1. A cross section through the line C-C is illustrated in FIG. 16. The width 42 of the wedge body 1 from the edges 14 of the sides 16 is between 1.0 mm and 1.60 mm. The height 43 of the wedge between the ridge and the edge 14 of the sides 16 is between 1.6 mm and 2.4 mm.

Figure 17:
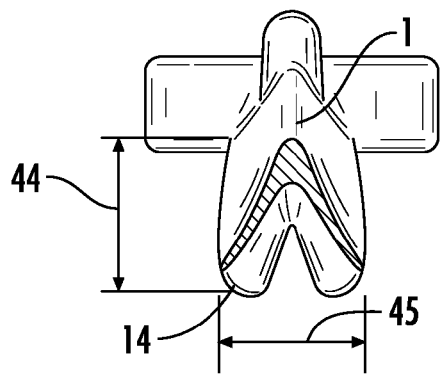
FIG. 17 is a cross section along the line D-D of the dental wedge of FIG. 13.
Figure 18:
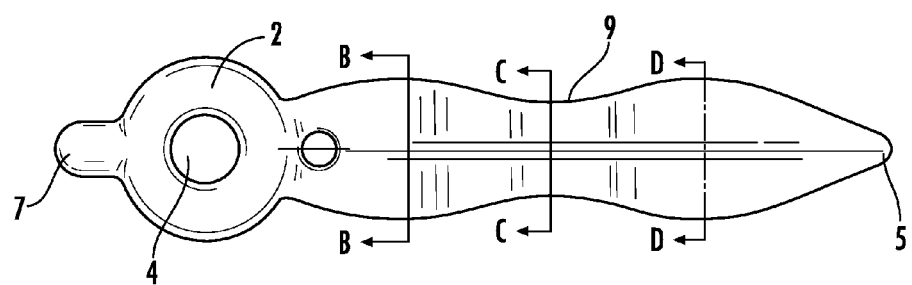
FIG. 18 is a plan view of a further alternate embodiment of the dental wedge of the present invention.
Figure 19:
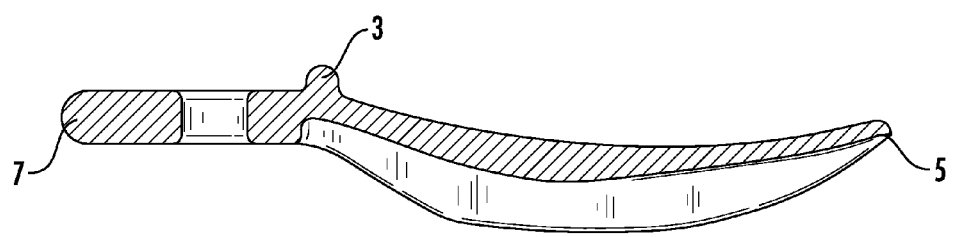
FIG. 19 is a partial cross section side view of the dental wedge of FIG. 18.

The second width is between the mid-portion 9 and the tip end 8 of the body. A cross section through the line D-D is illustrated in FIG. 17. The width 45 of the wedge body 1 from the edges 14 of the sides 16 is between 1.6 mm and 2.4 mm. The height 44 of the wedge between the ridge and the edge 14 of the sides 16 is between 1.6 mm and 2.4 mm.

Figure 15:
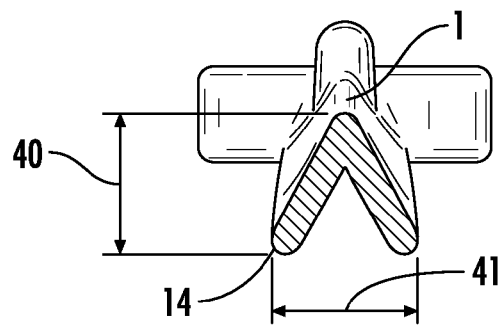
FIG. 15 is a cross section along the line B-B of the dental wedge of FIG. 13.

The third width is between the mid-portion 9 and the handle end 11 of the body. A cross section through the line B-B is illustrated in FIG. 15. The width 41 of the wedge body 1 from the edges 14 of the sides 16 is between 1.6 mm and 2.4 mm. The height 40 of the wedge between the ridge and the edge 14 of the sides 16 is between 1.6 mm and 2.4 mm.

Figure 20:
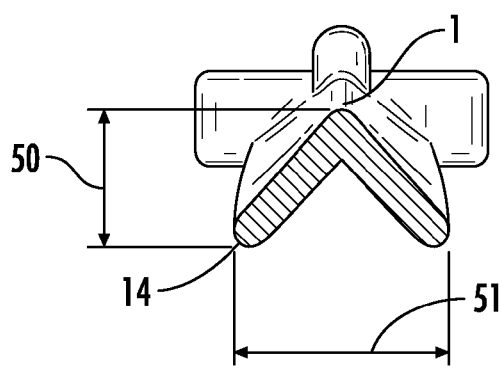
FIG. 20 is a cross section along the line B-B of the dental wedge of FIG. 18.
Figure 21:
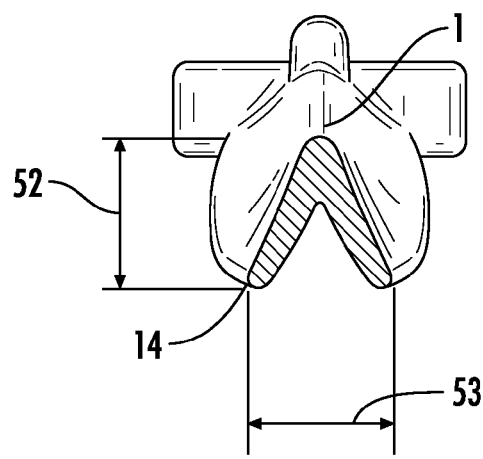
FIG. 21 is a cross section along the line C-C of the dental wedge of FIG. 18.

Referring to FIGS. 18 to 22 a large size wedge is illustrated. The mid portion 9 is the narrowest portion of the body. A cross section through the line C-C is illustrated in FIG. 21 and the width 42 of the wedge body 1 from the edges 14 of the sides 16 is between 1.6 mm and 2.4 mm. The height 43 of the wedge between the ridge and the edge 14 of the sides 16 is between 1.6 mm and 2.4 mm.

Figure 22:
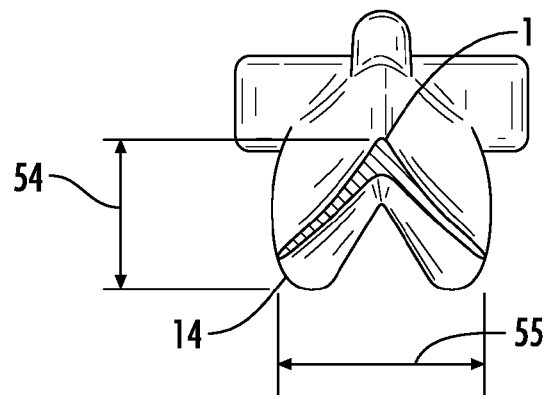
FIG. 22 is a cross section along the line D-D of the dental wedge of FIG. 18.

The second width is between the mid-portion 9 and the tip end 8 of the body. A cross section through the line D-D is illustrated in FIG. 22. The width 45 of the wedge body 1 from the edges 14 of the sides 16 is between 2.4 trim and 3.6 mm. The height 44 of the wedge between the ridge and the edge 14 of the sides 16 is between 1.6 mm and 2.4 mm.

The third width is between the mid-portion 9 and the handle end 11 of the body. A cross section through the line B-B is illustrated in FIG. 20. The width 41 of the wedge body 1 from the edges 14 of the sides 16 is between mm and mm. The height 40 of the wedge between the ridge and the edge 14 of the sides 16 is between 1.6 mm and 2.4 mm.

Figure 23:
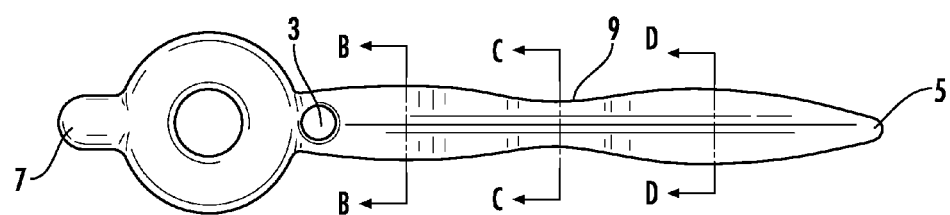
FIG. 23 is a plan view of a further alternate embodiment of the dental wedge of the present invention.
Figure 24:
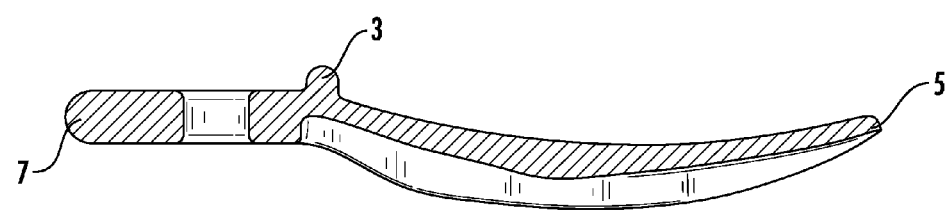
FIG. 24 is a partial cross section side view of the dental wedge of FIG. 23.
Figure 26:
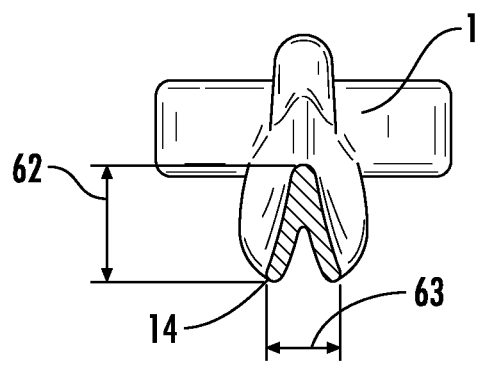
FIG. 26 is a cross section along the line C-C of the dental wedge of FIG. 23.

Referring to FIGS. 23 to 17 a small size wedge is illustrated. The mid portion 9 is the narrowest portion of the body. A cross section through the line C-C is illustrated in FIG. 26 and the width 42 of the wedge body 1 from the edges 14 of the sides 16 is between 0.8 mm and 1.2 mm. The height 43 of the wedge between the ridge and the edge 14 of the sides 16 is between 1.2 mm and 1.8 mm.

Figure 27:
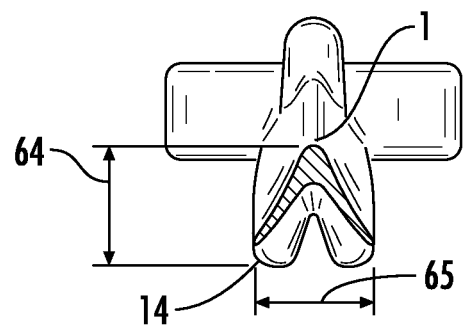
FIG. 27 is a cross section along the line D-D of the dental wedge of FIG. 23.

The second width is between the mid-portion 9 and the tip end 8 of the body. A cross section through the line D-D is illustrated in FIG. 27. The width 45 of the wedge body 1 from the edges 14 of the sides 16 is between 1.3 mm and 2.0 mm. The height 44 of the wedge between the ridge and the edge 14 of the sides 16 is between 1.2 mm and 1.8 mm.

Figure 25:
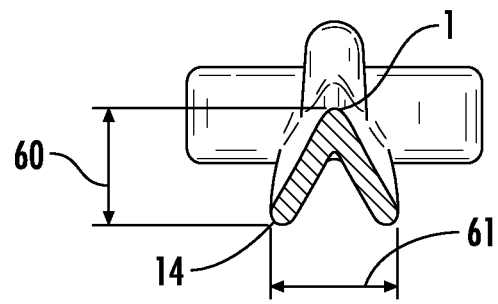
FIG. 25 is a cross section along the line B-B of the dental wedge of FIG. 23.

The third width is between the mid-portion 9 and the handle end 11 of the body. A cross section through the line B-B is illustrated in FIG. 25. The width 41 of the wedge body 1 from the edges 14 of the sides 16 is between 1.3 mm and 2.0 mm. The height 40 of the wedge between the ridge and the edge 14 of the sides 16 is between 1.2 mm and 1.8 mm.

Figure 11:
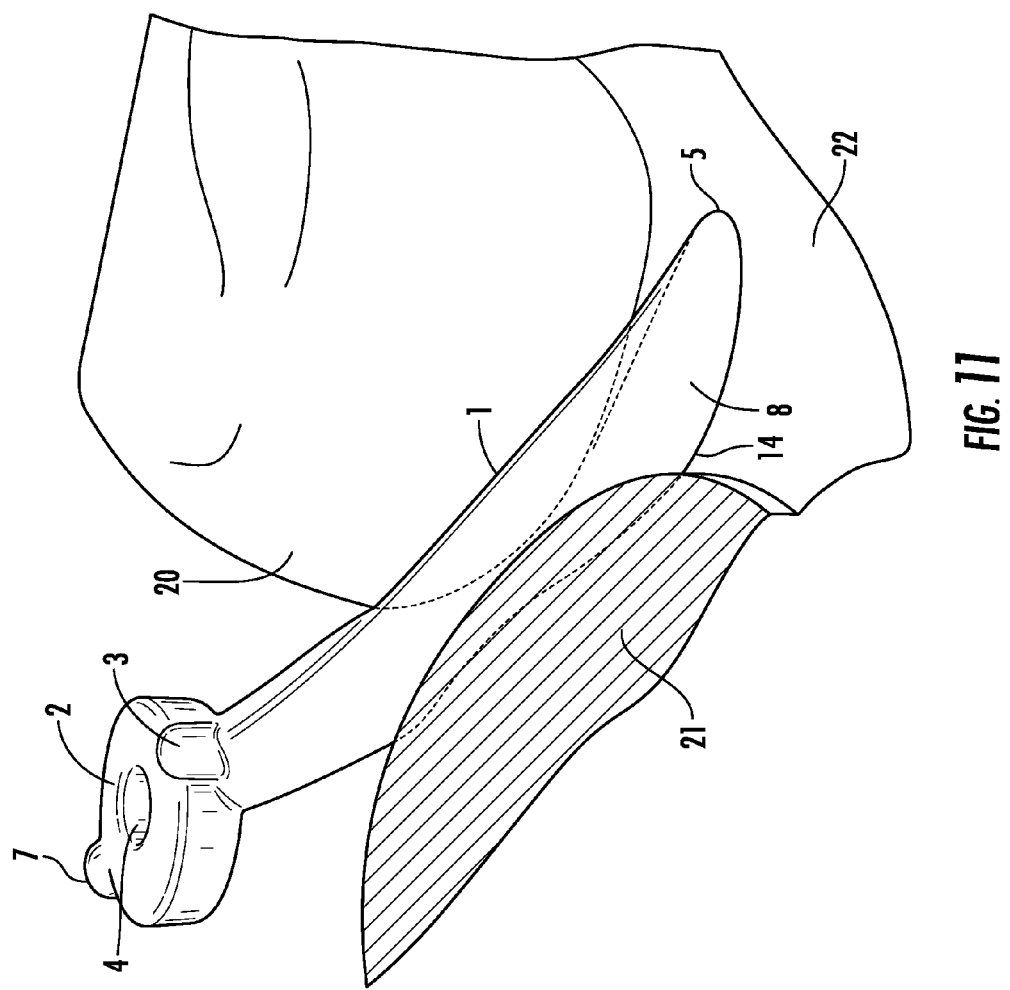
FIG. 11 is a view of dental wedge of the present invention in use, illustrated with a partial cross section of a tooth.
Figure 12:
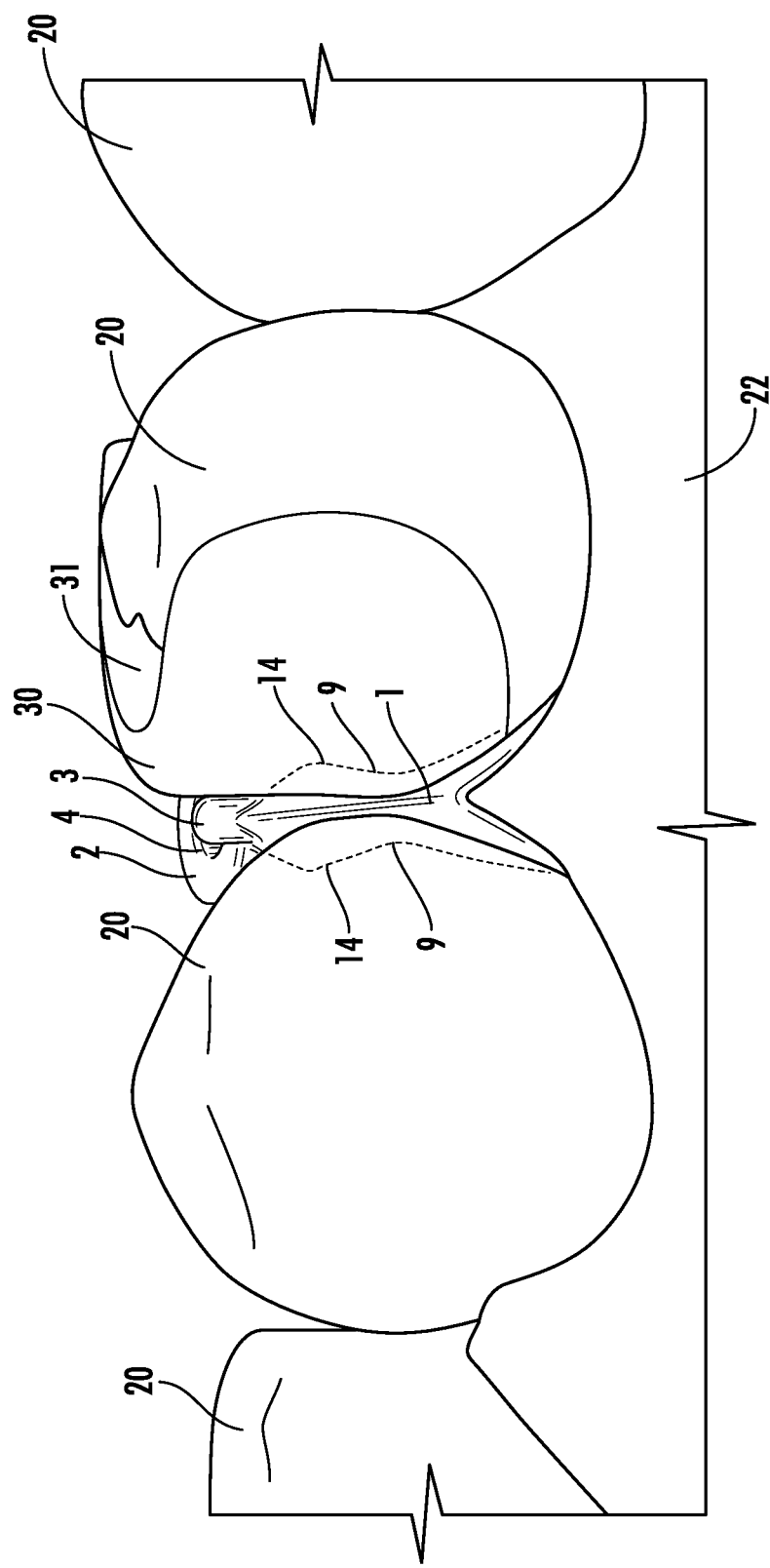
FIG. 12 is a side view of the dental wedge of the present invention in use.
Figure 13:
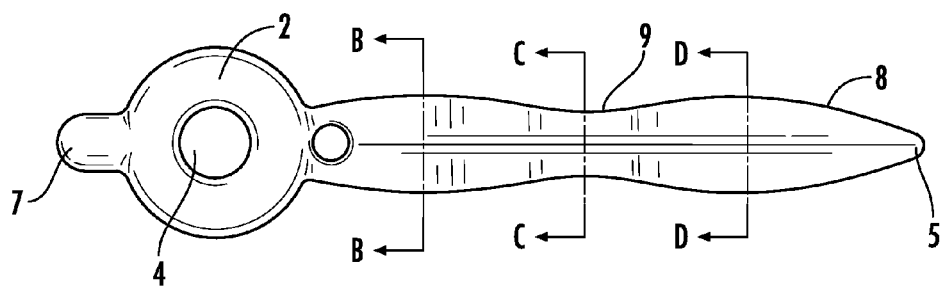
FIG. 13 is a plan view of an alternate embodiment of the dental wedge of the present invention.
Figure 14:
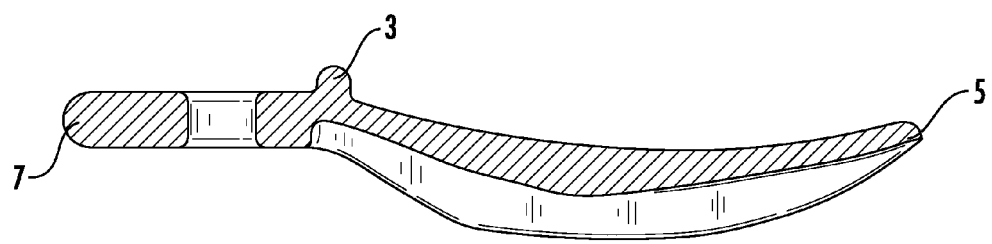
FIG. 14 is a partial cross section side view of the dental wedge of FIG. 13.

Referring to FIGS. 11 and 12 the wedge is used in the following manner. A dentist positions their preferred type of matrix band 30 or sectional matrix on the tooth 20 in the usual manner. The handle 2 of the wedge is held with a pair of pin-tweezers not illustrated (described in New Zealand Patent 537463) or conventional tweezers. The wedge is then placed between the matrix band 30 and the neighbouring tooth 20 in a conventional manner. After the restorative material has been placed, the wedge is removed by either grasping the hole 4 with the pin-tweezers or gripping the wedge body 1 close to the projection 3 using conventional tweezers. This projection 3 helps prevent the tweezers from slipping when the wedge is being removed.

The wedge is advantageous over the prior art in that the mid-section 9 of the wedge is flexible, which allowing the wedge to seal the gingival margin of the matrix band at both the buccal and lingual side. The handle 2 with a hole 4 provides an excellent means to hold the wedge, particularly with pin-tweezers.

The curvature of the wedge body 1 enables the dentist to insert the wedge into the inter-proximal space without it piercing the gingival papilla on the other side. The use of a V-shaped cross-section increases the wedge flexibility and provides a space for the gingival tissues.

The invention claimed is:

1. A dental wedge, for use in the inter-proximal space between adjacent teeth, said dental wedge comprising:
    a tapering section ending at a tip;
    a body section adjacent to and extending from said tapering section;
    said body section having a cross-section formed by a first and a second flexible spaced sidewall, each of said first and second sidewall having a bottom edge, and each of said first and second sidewall converging towards one another away from the bottom edge and defining an open-sided hollow space therebetween, wherein flexing of said first and second sidewall of the body section allows the wedge to adapt to various contours of the inter-proximal space and allows gingival tissues to extend into said hollow space, and
    said body section including a first widened section adjacent the tapering section, a narrowing mid-portion adjacent the first widened section, and a second widened section adjacent the narrowing mid-portion, wherein the bottom edge of said first and second sidewall follow a wave-like path through the first widened section, the narrowing mid-portion, and the second widened section, wherein each of the bottom edges defines a profile having a generally concave shape at the narrowing mid-portion.

2. The dental wedge of claim 1, wherein each of the bottom edges defines a convex shape at the first widened section and the second widened section.

3. The dental wedge of claim 1, wherein the cross-section formed by the first and the second flexible spaced sidewall is an inverted V-shaped cross-section.

4. The dental wedge of claim 1, further comprising a ridge, wherein the first and second sidewall converge at the ridge.

5. The dental wedge of claim 1, wherein the body section, as viewed from a side is of substantially uniform depth.

6. The dental wedge of claim 1, wherein said wedge includes a handle and said body section extends between said tapering section and said handle.

7. The dental wedge of claim 6, wherein said handle includes a flat member with a hole there through.

8. The dental wedge of claim 7, wherein a contour of said body section transitions smoothly along a length of the body section.

9. The dental wedge of claim 1, wherein the V-shaped cross-section is continuous along a length of said body section and said tapering section.

10. The dental wedge of claim 9, wherein said tip is blunt, with a leading end radius greater than 0.2 mm, and being at least 1.3 mm wide 3 mm from said tip.

11. The dental wedge of claim 1, wherein said side walls flex elastically toward each other during insertion through a space narrower than a widest width of said body section.

12. The dental wedge of claim 1, wherein a length of said body section is between 10 mm and 20 mm.

13. The dental wedge of claim 1, wherein a maximum width of said body section is between 0.8 mm and 3.6 mm.

14. The dental wedge of claim 1, wherein a height of the cross-section of said body section is between 1.2 mm and 2.4 mm.

15. The dental wedge of claim 1, wherein said V-shaped cross-section includes an angle of between 50° and 25° at a most open cross-section.

16. The dental wedge of claim 15, wherein said V-shaped cross-section at said narrowing mid-portion includes an angle of between 35° and 15°.

17. The dental wedge of claim 1, wherein said V-shaped cross-section at said narrowing mid-portion includes an angle of between 35° and 15°.

18. The dental wedge of claim 1, wherein the hollow space is a variable size, adapting in size to the flexing of the sidewalls.

19. The dental wedge of claim 1, wherein the dental wedge is formed from a single material.

20. The dental wedge of claim 1, wherein the flexible sidewalls are substantially planar.

21. The dental wedge of claim 1, wherein the first and second sidewall bottom edges of the first and second widened sections, and the narrowing mid-portion transition smoothly between the sections.

22. The dental wedge of claim 1, wherein the width of the open-sided hollow space between said first and second sidewall of the first and second widened sections is substantially equal.

23. The dental wedge of claim 1, wherein the first and second sidewalls are steeper at said mid-portion than at regions toward either end of the dental wedge.

24. The dental wedge of claim 1, wherein said body section, viewed from a side, has a curved profile, rising to the taper section and curved downward toward said mid-portion.

25. The dental wedge of claim 24, wherein at its lowest point along the wedge, the upper edge of the wedge is spaced between 0.6 mm and 1.1 mm from a line extending between the upper edge of the wedge adjacent the tip and the upper edge of the wedge adjacent the handle.

* * * * *